United States Patent [19]
Bakale et al.

[11] Patent Number: 5,973,182
[45] Date of Patent: Oct. 26, 1999

[54] CARBONATE INTERMEDIATES USEFUL IN THE PREPARATION OF OPTICALLY ACTIVE CYCLOHEXYLPHENYLGLYCOLATE ESTERS

[75] Inventors: Roger P. Bakale, Shrewsbury, Mass.; Jorge L. Lopez, San Juan, Puerto Rico; Francis X. McConville, Grafton, Mass.; Charles P. Vandenbossche, Marlborough, Mass.; Chris Hugh Senanayake, Shrewsbury, Mass.

[73] Assignee: Sepracor Inc., Marlborough, Mass.

[21] Appl. No.: 09/177,456

[22] Filed: Oct. 22, 1998

[51] Int. Cl.$^6$ ...................................................... C07C 69/96
[52] U.S. Cl. ........................................... 558/267; 558/275
[58] Field of Search ..................................... 558/267, 275

[56] References Cited

U.S. PATENT DOCUMENTS 2,837,525  6/1958  Ruddy et al. ......................... 260/293.4

FOREIGN PATENT DOCUMENTS 708370  of 1954  United Kingdom .
750156  of 1956  United Kingdom .
940540  of 1963  United Kingdom .

OTHER PUBLICATIONS

Barlow et al., "Studies on the Stereospecificity of Closely Related Compounds Which Block Postganglionic Acetylcholine Receptors in the Guinea–Pig Ileum", J. Medic. Chem. 16, 439–446 (1973).

L. Schjelderup and A.J. Aasen, "The Absolute Configuration of Oxyphencyclimine, a Parasympatholytic Drug, of Both Enantiomers", Acta Chem. Scand. B 40, 601–603 (1986).

Inch et al., "Asymmetric Synthesis: Part III. Stereospecific Synthesis of (R)–2–Hydroxy–2–Phenylpropionic (R)–and (S)–2–Cyclohexyl–2–hydroxy–2phenylacetic Acid. Configurational Relationship between (R)(–)–2–Hydroxy–2–phenylpropionic Acid and (S) (+)–2–Phenylpropionic Acid", J. Chem. Soc. (C), 1693–1699 (1968).

Majewski et al., ;"Anticholinergic Agents. Esters of 4–Dialkyl– (or 4–Polymethylene–) amino–2–butynols", J. Chem. Soc., 19–720 (1965).

S.G. Kuznetsov and Z.I. Bobysheva, "Optical Isomers of Some Cholinolytic Substances", J. General Chem. (US (1962).

Take et al., "Agents for the Treatment of Overactive Detrusor.III. Synthesis and Structure–Activi Relationships of N–(4–Amino–2–butynyl)acetamide Derivatives", Chem. Pharm. Bull., 40 1415–1423 (1992).

K.G. Feitsma, "Enantiomeren Van Oxyfenoniumbromide", Pharm. Weekbl. 124, 383–387 (1989).

Atkinson et al., "Parasympatholytic (Anticholinergic) Esters of the Isomeric 2–Tropanols. 1. Glycolate", J. Med. Chem. 20, 1612–1617 (1977).

Katchur et al., "R and S Enantiomers of Oxybutynin: Pharmacological Effects in Guinea Pig Bladder and Intestine", J. Pharmacol. Exp. Ther., 247, 867–872 (1988).

*Primary Examiner*—Michael G. Ambrose
*Attorney, Agent, or Firm*—Heslin & ROthenberg, P.C.

[57] ABSTRACT

A process for the preparation of optically active phenylcyclohexylglycolate esters is described. The process utilizes carboxylic acid activation to couple (R)- or (S)-cyclohexylphenylglycolic acid (CHPGA) with 4-N,N-diethylamino butynol or other propargyl alcohol derivatives. The preparation of the hydrochloride salt is also described. In addition, a resolution process employing tyrosine methyl ester enantiomers for preparing a single enantiomer of CHPGA from racemic CHPGA is disclosed.

4 Claims, No Drawings

CARBONATE INTERMEDIATES USEFUL IN THE PREPARATION OF OPTICALLY ACTIVE CYCLOHEXYLPHENYLGLYCOLATE ESTERS

FIELD OF THE INVENTION

The present invention relates to a method for resolving cyclohexylphenyl glycolic acid and the preparation of optically active phenylcyclohexylglycolate esters.

BACKGROUND OF THE INVENTION

Cyclohexylphenyl glycolic acid (also referred to herein as "CHPGA") is used as a starting material for manufacturing compounds that have important biological and therapeutic activities. Such compounds include, for example, oxphencyclimine, oxyphenonium bromide, oxypyrronium bromide, oxysonium iodide, oxybutynin (4-diethylamino-2-butynyl phenylcyclohexylglycolate) and its metabolites, such as desethyloxybutynin (4-ethylamino-2-butynyl phenylcyclohexylglycolate). The important relation between stereochemistry and biological activity is well known. For example, the (S)-enantiomers of oxybutynin and desethyloxybutynin have been shown to provide a superior therapy in treating urinary incontinence, as disclosed in U.S. Pat. Nos. 5,532,278 and 5,677,346. The (R) enantiomer of oxybutynin has also been suggested to be a useful drug candidate. [Noronha-Blob et al., *J Pharmacol Exp. her.* 256, 562–567 (1991)].

Racemic CHPGA is generally prepared by one of two methods: (1) selective hydrogenation of phenyl mandelic acid or of phenyl mandelate esters, as shown in Scheme 1; or (2) cyclohexyl magnesium halide addition to phenylglyoxylate as shown in Scheme 2.

Scheme 1.

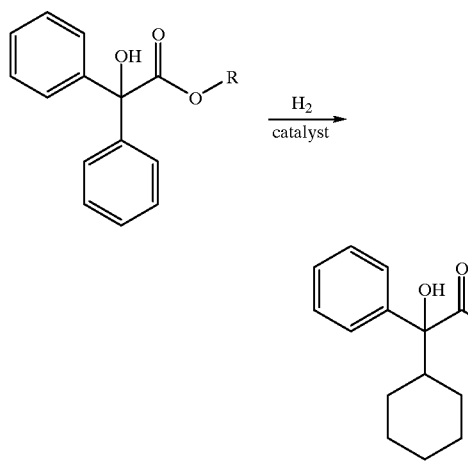

R is hydrogen or lower alkyl.

Scheme 2.

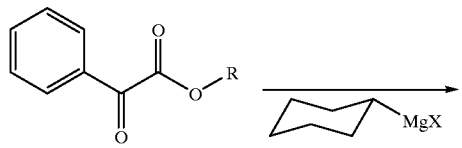

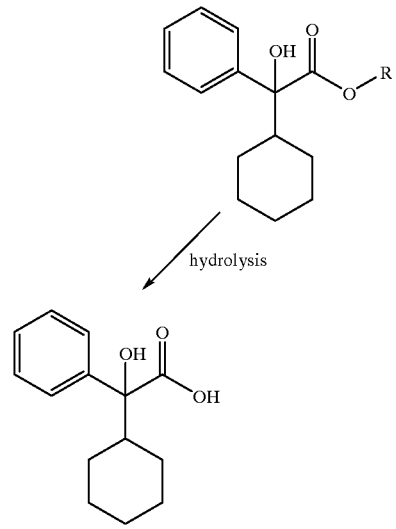

Asymmetric synthesis of individual enantiomers of CHPGA has been approached along the lines of Scheme 2, by Grignard addition to a chiral auxiliary ester of glyoxylic acid to give a diastereomeric mixture of esters. In addition, multiple step asymmetric synthesis of (R)-CHPGA from (D)-arabinose using Grignard reagents has been reported. In general, simple primary alkyl or phenyl Grignard (or alkyllithium) reagents are used for the addition, and the addition of inorganic salts (e.g. $ZnCl_2$) appears to increase the diastereoselectivity of the products.

As outlined in Scheme 3 below, the simple chiral ester wherein R* is the residue of a chiral alcohol, can be directly converted to chiral drugs or drug candidates by trans-esterification (R'=acetate), or hydrolyzed to yield chiral CHPGA (R'=H).

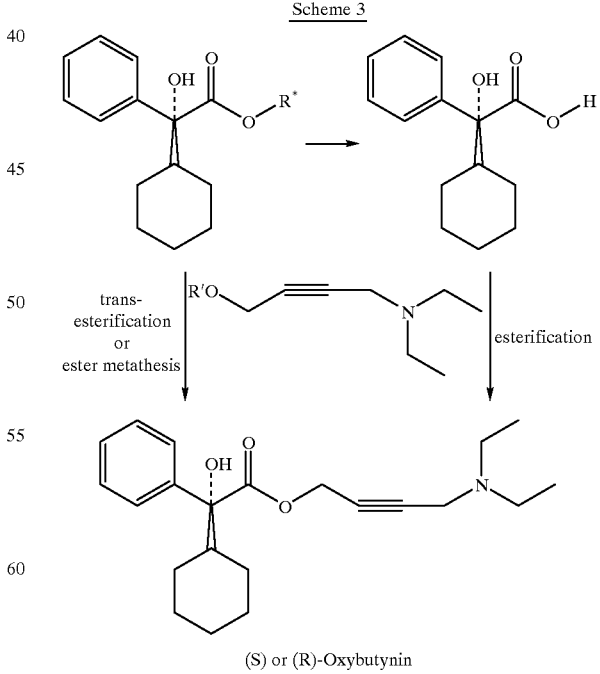

While the aforementioned asymmetric synthetic methods are adequate for many purposes, the chemical yields are in some cases poor, and the stereoselectivity is not always high. Also, the chiral auxiliary reagents that give good yields and higher stereoselectivity are often quite expensive. Thus, these processes are often cost prohibitive for use in commercial scale production of chiral pharmaceutical compounds.

A potential alternative to asymmetric synthesis is resolution of racemic CHPGA. This has been accomplished on an analytical scale using resolving agents such as ephedrine, quinine, and (+) and (−)-amphetamine. However, such resolving agents are expensive, making known processes for resolution as impractical as known asymmetric syntheses. In addition, resolution processes using these agents provide poor stereoselectivity. The poor stereoselectivity necessitates multiple recrystallization steps to isolate the single CHPGA enantiomer, which adds to the production costs of chiral pharmaceuticals made from these precursors. Therefore, a need exists for a more efficient and economic method for preparing the single enantiomers of CHPGA on a commercial scale.

As shown above in Scheme 3, separated enantiomers of CHPGA can be esterified to produce (S) and (R)-oxybutynin. Such a process was reported by Kachur et al. in *J.Pharmacol. Exper. Ther.* 247, 867–872 (1988) using the method of Mitsunobu. Briefly, the (R) and (S) enantiomers of oxybutynin were prepared by directly coupling the separated CHPGA enantiomers with 1-N,N-diethylaminobutynol using diethyl azodicarboxylate and triphenyl phosphine as coupling reagents. However, the Mitsunobu reaction suffers from many disadvantages. For example, the aforementioned coupling reagents are quite expensive, and the reaction results in the formation of triphenylphosphine oxide, a by-product which is very difficult to remove. Thus, yield is often low, and extensive purification is needed to isolate the oxybutynin enantiomer. For these reasons, direct coupling using this prior art process is unattractive on a commercial scale.

A more efficient and economic method for producing chiral oxybutynin and its related compounds on an industrial scale is therefore desirable. A preparative scale method for producing the enantiomers of CHPGA for use as precursors, as well as a more convenient and inexpensive method for subsequent esterification would meet this need. Such methods should provide high purity compounds in high chemical yields with few processing steps, making them practical for use in the commercial production of optically active oxybutynin and related compounds.

SUMMARY OF THE INVENTION

The above need is satisfied, the limitations of the prior art overcome, and other benefits realized in accordance with the principles of the present invention, which in one aspect relates to a process for the resolution of racemic cyclohexylphenyl glycolic acid (CHPGA) into its individual enantiomers having formulae $I_r$ and $I_s$.

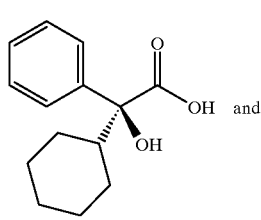

$I_r$ and

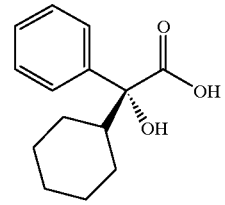

$I_s$

The process of the invention for preparing a single enantiomer of cyclohexylphenyl glycolic acid comprises:
(a) providing a solution comprising racemic cyclohexylphenyl glycolic acid and a single enantiomer of tyrosine methyl ester;
(b) driving a salt of primarily one diastereomer out of solution;
(c) separating the diastereomeric salt from the solution; and
(d) liberating the single enantiomer of cyclohexylphenyl glycolic acid from the diastereomeric salt.

In another aspect, the invention relates to the diastereomeric salts, (S)-cyclohexylphenyl glycolic acid L-tyrosine methyl ester salt and (R)-cyclohexylphenyl glycolic acid D-tyrosine methyl ester salt, which crystallize when L-tyrosine methyl ester or D-tyrosine methyl ester, respectively, is combined with racemic cyclohexylphenyl glycolic acid in the above process.

In another aspect, the invention relates to a process for preparing a single enantiomer of structure (II)

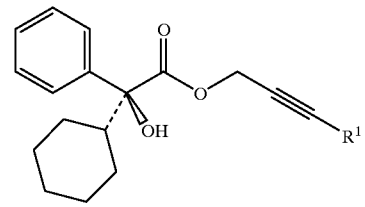

(II)

wherein $R^1$ is chosen from the group of hydrogen or —$CH_2R^2$, wherein $R^2$ is chosen from the group of azide, hydroxy, halo, or —$NR^3R^4$, wherein $R^3$ and $R^4$ are each independently hydrogen or lower alkyl. The synthetic method directly couples an enantiomer of CHPGA with a propargyl alcohol derivative to produce a single enantiomer of a propargyl ester of cylclohexylphenylglycolate. The method comprises:
(a) activating the carboxy group of a single enantiomer of cyclohexylphenyl glycolic acid to form an activated carboxy compound; and
(b) adding to the activated carboxy compound a sidechain propargyl alcohol derivative of structure (III)

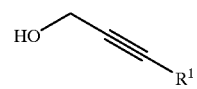

(III)

wherein $R^1$ is as previously defined to produce the single enantiomer of structure (II).

In yet another aspect, the invention relates to the preparation of the hydrochloride salt of a single enantiomer of structure (II) above, in which $R^1$ is —$CH_2R^{2a}$ and $R^{2a}$ is —$NR^3R^4$. The process comprises preparing the single enantiomer of structure (II) according to the method set forth above, then separating the organic solvent containing the single enantiomer of structure (II) from the reaction mixture. The organic solvent is then exchanged with ethyl acetate to produce an ethyl acetate solution containing the single enantiomer of structure (II). The ethyl acetate solution is then concentrated and dried to contain about 20–25% by weight single enantiomer of structure (II) and ≦0.3% by weight water. Methyl t-butyl ether is then added to provide an ethyl acetate/t-butyl ether solution, wherein the concentration of the single enantiomer of structure (II) is reduced by about one third. A mixture of HCl in ethanol is added to the ethyl acetate/t-butyl ether solution to form a hydrochloride salt of the single enantiomer of structure (II).

In yet another aspect, the invention relates to the preparation of a single enantiomer of structure (II) using the aforementioned coupling process in which the single enantiomer of cyclohexylphenyl glycolic acid of structure (I) is obtained using the resolution process outlined above.

In another aspect, the invention relates to intermediates of the formulae:

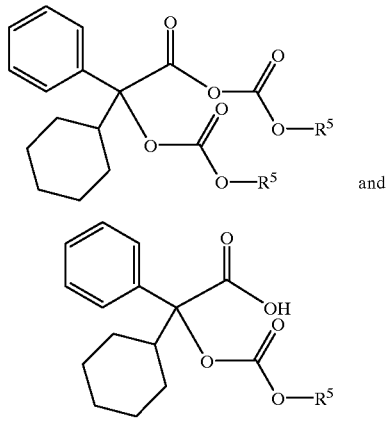

and wherein $R^5$ is alkyl or alkenyl of one to ten carbons. Preferably $R^5$ is isobutyl. Both intermediates are useful in the preparation of optically pure isomers of CHPGA esters, such as oxybutynin.

Advantages of the present resolution process over the prior art include: higher efficiency, fewer processing steps, and a more readily available resolving agent. Previous resolution processes utilizing ephedrine as the resolving agent, for example, require a multi-step crystallization process to obtain (S)-CHPGA (e.g., 98–99% ee). The overall yield of these steps is approximately 30%. The process described herein using an enantiomer of tyrosine methyl ester gives a 42% yield of 99% ee diastereomer in a single resolution step. (Note that the theoretical maximum yield for a resolution of a racemate is 50%.) In addition, the use and transport of ephedrine and its derivatives have come under increasing scrutiny by the DEA and other world drug enforcement agencies in recent years, driving up the price and making availability of bulk supplies unreliable. No such regulatory restrictions apply to L-tyrosine or its derivatives.

The advantages of the present synthetic method for producing oxybutynin and its analogs over the prior art methods include: a one step process from chiral CHPGA without isolation of any intermediates, and an improvement in yield and quality over the transesterification process shown in Scheme 3. The process can also be used to produce a variety of analogs not available through transesterification or alkoxy radical couplings.

DETAILED DESCRIPTION

The graphic representations of racemic, ambiscalemnic and scalemic or enantiomerically pure compounds used herein are taken from Maehr, *J. Chem. Ed.* 62, 114–120 (1985): solid and broken wedges are used to denote the absolute configuration of a chiral element; wavy lines indicate disavowal of any stereochemical implication which the bond it represents could generate, commonly a racemic mixture; and wedge outlines and dotted or broken lines denote enantiomerically pure compounds of indeterminate absolute configuration. Thus, for example, formula (I) is intended to encompass both of the enantiomerically pure cyclohexylphenyl glycolic acids:

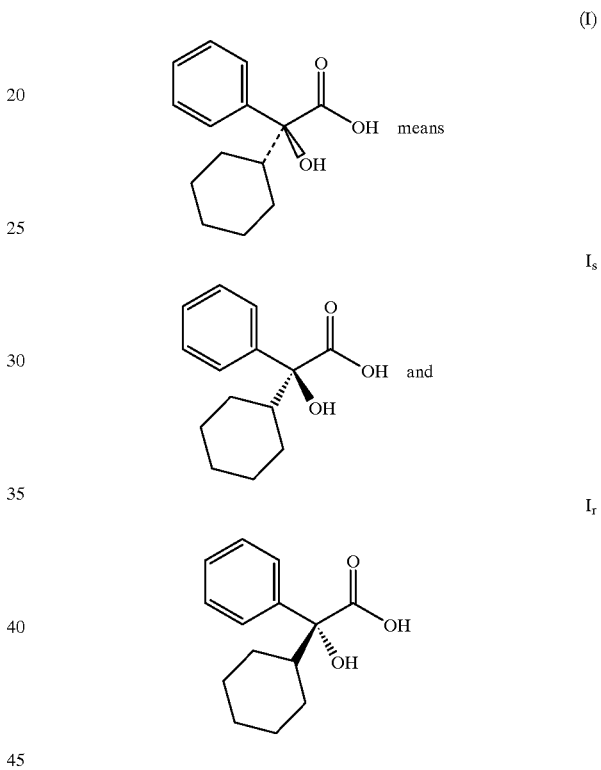

The term "enantiomeric excess" is well known in the art and is defined for a resolution of ab→a+b as $$ee_a = \left(\frac{\text{conc. of } a - \text{conc. of } b}{\text{conc. of } a + \text{conc. of } b}\right) \times 100$$

The term "enantiomeric excess" is related to the older term "optical purity" in that both are measures of the same phenomenon. The value of ee will be a number from 0 to 100, zero being racermic and 100 being pure, single enantiomer. A compound which in the past might have been called 98% optically pure is now more precisely described as 96% ee.; in other words, a 90% e.e. reflects the presence of 95% of one enantiomer and 5% of the other in the material in question.

"Alkyl", as used herein, refers to saturated hydrocarbon residues containing twenty or fewer carbons in straight or branched chains, as well as cyclic structures. "Lower alkyl" is 6 or fewer carbons. The term "% by weight" is interchangeable with and has the same meaning as "wt %". The term "equiv.", as used herein, refers to molar equivalents.

Unless otherwise indicated, the reactants and reagents used in the processes of the present invention described herein are readily available materials. Such materials can be conveniently prepared with conventional preparatory procedures or obtained from commercial sources.

As outlined above, the present process for preparing a single enantiomer of cyclohexylphenyl glycolic acid comprises:

(a) providing a solution comprising racemic cyclohexylphenyl glycolic acid and a single enantiomer of tyrosine methyl ester;

(b) driving a salt of primarily one diastereomer out of solution;

(c) separating the diastereomeric salt from the solution; and (d) liberating the single enantiomer of cyclohexylphenyl glycolic acid from the diastereomeric salt.

In one embodiment, the solution of step (a) is accomplished by dissolving a mixture of racemic cyclohexylphenyl glycolic acid and a single enantiomer of tyrosine methyl ester in acetonitrile and water by heating to form a solution and step (b) is accomplished by allowing the solution to cool, whereby a salt of primarily one diastereomer crystallizes. Liberation of the single enantiomer of cyclohexylphenyl glycolic acid from the diastereomeric salt may be accomplished by adding the diastereomeric salt to a mixture of toluene and aqueous mineral acid. The resulting toluene solution may then be reduced in volume and cooled. The single enantiomer of cyclohexylphenyl glycolic acid product may then be filtered off. In addition, if desired, tyrosine methyl ester may be recovered.

The aspect of the invention relating to a synthetic method for directly coupling an enantiomer of CHPGA with a propargyl alcohol derivative to produce a single enantiomer of a propargyl ester of cylclohexylphenylglycolate includes a step in which the carboxy group of a single enantiomer of cyclohexylphenyl glycolic acid is activated to form an activated carboxy compound. Methods for activating carboxyl toward displacement by alcohols are known in the art for preparing esters. However, since the starting material in this case contains an unprotected alcohol function, it is surprising that the activation and condensation can be carried out with sufficient specificity to provide a product which is not an intractable mixture of self-condensation products of the glycolic acid component. In the preferred embodiment of the invention, the single enantiomer of cyclohexylphenyl glycolic acid is reacted with an alkyl chloroformate in an organic solvent to form a mixed anhydride; and a sidechain propargyl alcohol derivative of structure (III) is added to the mixed anhydride. In a preferred embodiment, the alkyl chloroformate is isobutylchloroformate.

(S) OR (R)-CYLOHEXYLPHENYL GLYCOLIC ACID VIA RESOLUTION

The resolution process of the present invention provides an inexpensive and efficient method for preparing a single enantiomer from racemic CHPGA via the formation of the diastereomeric salt with (L) or (D)-tyrosine methyl ester, also referred to herein as "(L) or (D)-TME". The process consists of three parts, which are depicted and described below: Part 1: Preparation of (S)-CHPGA-(L)-TME diastereomeric salt or (R)-CHPGA-(D)-TME diastereomeric salt; Part 2: Preparation of (S) or (R) CHPGA; and Part 3—Recovery of (L) or (D)-tyrosine methyl ester. The ability to recover the resolving agent in high yield is an advantageous feature of the process of the invention. It greatly reduces cost by allowing recycling of the resolving agent.

For ease in understanding, the diastereomeric salt, (S)-CHPGA-(L)-TME, and the pure enantiomer (S)-CHPGA are depicted in the reactions below. However, the (R) enantiomeric series could instead be depicted and is similarly produced using the opposite enantiomer of TME.

Part 1: Preparation of (SL-CHPGA-(L)-Tyrosine Methyl Ester Diastereomer Salt

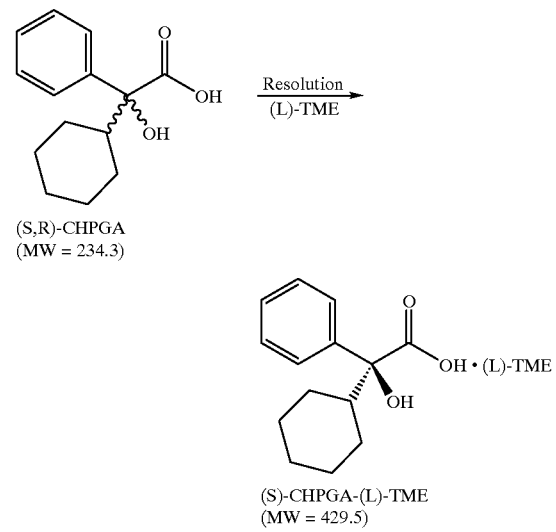

For use in the process of Part 1, the racemic starting material, (S,R)-cyclohexylphenyl glycolic acid (CHPGA) can be prepared by the process described above, i.e. (1) selective hydrogenation of phenyl mandelic acid or of phenyl mandelate esters or (2) cyclohexyl magnesium halide addition to phenylglyoxylate. Mandelic acid and phenylglyoxylic acid, also known as benzoylformic acid, are commercially available. Phenyl mandelic acid may be prepared by Grignard addition of phenyl magnesium bromide to diethyl oxalate followed by hydrolysis. The (L) enantiomer of tyrosine methyl ester is also readily available from commercial sources, as is (D)-tyrosine, which can then be esterified to produce (D)-tyrosine methyl ester using conventional techniques, such as acid-catalyzed esterification with methanol.

The diastereomer of the present process is produced by dissolving racemic CHPGA and an appropriate amount of an enantiomer of tyrosine methyl ester in a suitable solvent and then bringing about the insolubilization of one diastereomer. For example, racemic CHPGA and about 0.5 molar equivalents of (L)-tyrosine methyl ester or (D)-tyrosine methyl ester can be dissolved in a mixture of acetonitrile and water. When the solvent is about 10 wt % water in acetonitrile, solution may be achieved by heating, preferably by heating to reflux (approximately 78° C.). After heating the solution for a sufficient time to achieve complete dissolution, usually about 5 minutes at reflux, followed by cooling, preferably to about 0–5° C., the diastereomeric salt (S)-CHPGA-(L)-TME or (R)-CHPGA-(D)-TME, depending on the TME enantiomer used, crystallizes from solution. Better yields are obtained when the cooling temperature is maintained until crystallization of the diastereomer salt is complete, typically a period of about four hours. The salt crystals are then separated from the solution, for example by filtration. The crystalline product may be washed with solvent and dried. When the solvent is water/acetonitrile, drying under vacuum at about 40–50° C. is effective. The mother liquor stream may be saved for later racemization and recovery of residual CHPGA.

Part 2: Preparation of (S)-CHPGA

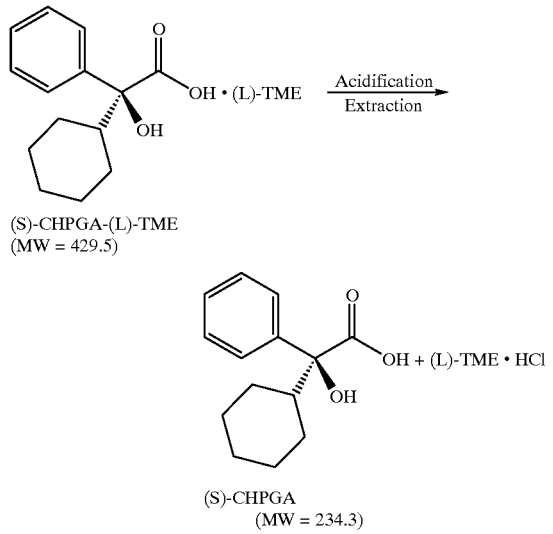

In Part 2, the CHPGA enantiomer produced, (S) or (R)-CHPGA, is liberated from the diastereomeric salt. For the preparation of (S)-CHPGA, the (S)-CHPGA-(L)-TME salt from Part 1 is added to and dissolved to form a solution which is about 15 wt % substrate in toluene. The solution is treated with an excess of dilute mineral acid, such as 1.1 equivalents of 0.5 M HCl or $H_2SO_4$. Upon dissolution of the diastereomeric salt, essentially all the TME enantiomer is converted to the hydrochloride salt. The diastereomeric salt mixture may be heated to about 40–50° C. for about 10 minutes to facilitate dissolution of the solids. A phase split yields an aqueous solution containing (L)-TME-HCl and an organic solution of (S)-CHPGA in toluene. The aqueous phase is separated from the organic solution and saved for recovery of the tryosine methyl ester in Step 3 below. A common method of separation, which may be used throughout the processes described herein, is gravitational settling followed by drainage of the aqueous phase through a tap in the bottom of the reaction vessel.

The toluene organic phase containing (S)-CHPGA may be washed a second time with mineral acid, as specified above, and heated. The organic phase and aqueous phase are then separated, and the aqueous phase is discarded along with the rag layer, i.e. the layer separating the two phases. The retained toluene organic phase is then preferably concentrated, typically by vacuum distillation, to a weight that is about 2.1 to 2.3 times the weight of the diastereomeric salt originally present, followed by gradual cooling to 0–5° C. to initiate crystallization of the single (S) enantiomer of CHPGA, as indicated by the formation of a thick slurry. The slurry is cooled for at least an hour to ensure that crystallization is complete, then filtered to isolate (S)-CHPGA. The (S)-CHPGA cake is then dried under vacuum while heating to a temperature of about (40–45° C.).

Part 3: Recovery of (L)-Tyrosine Methyl Ester

The aqueous phase containing (L)-TMNE-HCl or (D)-TME-HCl saved from Part 2 is cooled, preferably to about 0–5° C. While maintaining the cooling temperature, the aqueous solution is titrated with 0.5M NaOH to a pH of approximately 9.0. Typically, a thin slurry will form as the TME enantiomer precipitates. The TNIE enantiomer is isolated by filtration, washing with deionized water, and drying under vacuum at a temperature of about (40–50° C.).

The resolution process of the present invention set forth above is illustrated by, but not limited to, the following example:

EXAMPLE 1

Part 1: Preparation of (S)-CHPGA-(L)-Tyrosine Methyl Ester Diastereomer Salt

A 2-liter reactor was charged with 100.0 g racerric CHPGA, 41.7 g (L)-TME (0.5 equiv.), 549.2 g $CH_3CN$, and 54.8 g deionized water. The reaction mixture was heated to reflux at approximately 78° C. for about 5 min. The solution was then cooled to a temperature between 0–5° C. over a period of 2 hours and remained cooling (0–5° C.) for about 2 hours. The solution was filtered to isolate the (S)-CHPGA-(L)-TME diastereomeric salt, and the salt cake was washed with 130 g chilled (0–5° C.) $CH_3CN$. The salt cake was dried in vacuo at 40–50° C., and the residual solvent remaining in the cake was <0.5%. Yield=77.1 g (42.1 mole %); ee >99.0% (S).

Part 2: Preparation of (S)-CHPGA

A 1000 mL reactor was charged with 77.1 g (S)-CHPGA-(L)-TME from Part 1,447.0 g toluene, 339.2 g 0.5M HCl (1.1 equiv.) and heated to 40–50° C. while stirring until the solids dissolved (about 10 min). While maintaining the temperature at 40–50° C., the organic and aqueous phases separated after about 10 minutes. The phases were divided, and the aqueous (bottom) phase containing (L)-TME-HCl was saved for recovery in Part 3 below. Approximately 370 g aqueous phase was recovered.

To the toluene organic phase an additional 169.6 g 0.5M HCl (0.6 equiv.) were added, and the solution was heated to a temperature between 40–50° C. while stirring for about 10 minutes. The toluene and aqueous phases were allowed to separate (~10 min.), while maintaining the temperature between 40–50° C. The phases were divided, and the aqueous (bottom) phase and rag layer were discarded.

The organic phase was concentrated by vacuum distillation to a final weight of 168.0 g, then cooled to 0–5° C. over a period of about one hour during which time a thick slurry formed spontaneously. Agitation was adjusted as necessary. The slurry was cooled at 0–5° C. for an additional one hour. The slurry was filtered to recover the (S)-CHPGA. The (S)-CHPGA filter cake was dried in vacuo at 40–45° C., and the residual solvent remaining in the cake was <0.2%. Yield=35.8 g (85 mole %); ee >99.0%; chemical purity (% HPLC area) >99.0%.

Part 3: Recovery of (L)-Tyrosine Methyl Ester

A 2-liter vessel was charged with the aqueous phase saved from Part 2 (370 g). The solution was cooled to 0–5° C., and the cooling temperature was maintained while titrating with 0.5 M NaOH to a pH of 9.0±0.5 over approximately 30 min. A thin slurry formed as (L)-TME precipitated. The slurry was filtered, and the (L)-TME cake was washed with 154 g deionized water. The cake was dried in vacuo at 40–50° C., and the residual solvent remaining in the cake was <1.0%. Yield=30.5 g (L)-TME (87 mole %).

(S) OR (R)-OXYBUTYNIN AND RELATED COMPOUNDS VIA DIRECT COUPLING

The synthesis of a single enantiomer of oxybutyriin and oxybutynin analogs according to the present invention comprises coupling an enantiomer of cyclohexylphenyl glycolic acid with a propargyl alcohol derivative utilizing carboxylic acid activation. Optically active CHPGA may be prepared either by the resolution process described above or by asymmetric methods. The present invention also provides a process for converting the aforementioned enantiomers of oxybutynin and oxybutynin analogs to their corresponding hydrochloride salts.

The synthetic process consists of two reactions, which are depicted and described below: Part 1: Formation of the Mixed Anhydride; Part 2: Formation of (S) or (R) oxybutynin and its related compounds. Again for ease in understanding, the (S) enantiomeric series is depicted, although the (R) series is produced similarly.

Part 1: Formation of the Mixed Anhydride

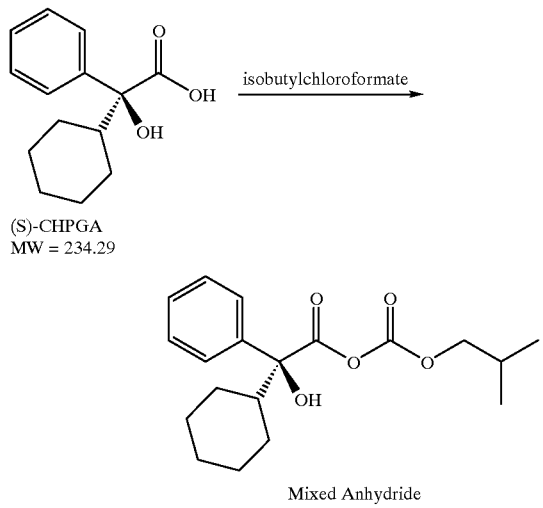

In Part 1, (S) or (R) cyclohexylphenyl glycolic acid (CHPGA) is reacted with an alkyl chloroformate in an organic solvent to form a mixed anhydride enantiomer, as shown above, which can then react to form the desired chiral product in Part 2 below.

It should be noted that, while mixed anhydrides are often employed for the synthesis of amides, their use for ester synthesis is quite unusual. It should also be noted that a surprising and unexpected aspect of the present process is that the mixed anhydride intermediate proceeds to a chiral product without affecting the tertiary carbinol of CHPGA, which would lead to impurity formation or racemization. One would expect reaction with an acyl halide at the benzylic hydroxyl resulting in the formation of a stable, but undesired compound, such as an ester. Alternatively, if the hydroxyl were activated (unintentionally) to form a good leaving group, as, for example, under acidic conditions, the dissociation of the leaving group would form a benzylic carbonium ion, leading to racemization. One would therefore expect a loss in optical activity of the oxybutynin or the extensive production of by-products. Surprisingly, the present process produces a high purity product, and no racemization is observed.

In the preparation of the mixed anhydride, two intermediates, in addition to the mixed anhydride shown above, were detected. The two were isolated and their structures were determined by NMR to be

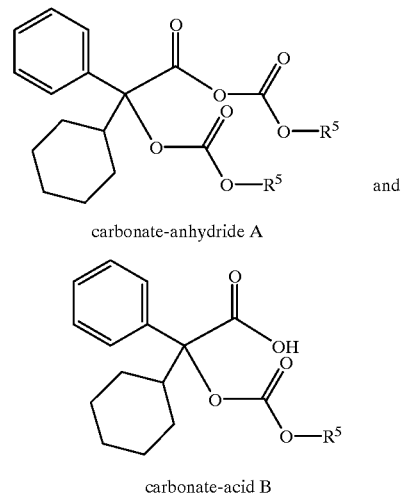

wherein $R^5$ was isobutyl. Both intermediates were smoothly converted to oxybutynin upon treatment with 4-N,N-DEB.

The reaction is preferably carried out in an inert atmosphere, such as nitrogen or argon, and the reaction solution is stirred using conventional techniques. In the depiction above, isobutyl chloroformate (IBCF) is shown as the preferred alkyl chloroformate for reaction with (S)-CHPGA forming the isobutyloxy mixed anhydride. However, other alkyl chloroformates, such as isopropenyl-chloroformate and 2-ethylhexylchloroformate, for example, may instead be used. The amount of alkyl chloroformate used in the reaction is preferably about 1.2 equivalents with respect to the CHPGA enantiomer.

Preferably, the reaction proceeds in the presence of a tertiary amine (2.5 equiv.), such as triethylamine (TEA), 4-N,N-dimethylarninopyridine (DMAP), pyridine, diisopropyl ethyl amine, or diethylmethyl amine, which scavenges the HCl produced. Organic solvents that may be used include, but are not limited to cyclohexane, heptane, toluene, tetrahydrofuran (THF), ethylene glycol dimethyl ether (DME), diethoxy methane (DEM), and methyl t-butyl ether (MTBE).

Part 2: Formation of (S) or (R)-Oxybutynin and its Analogs

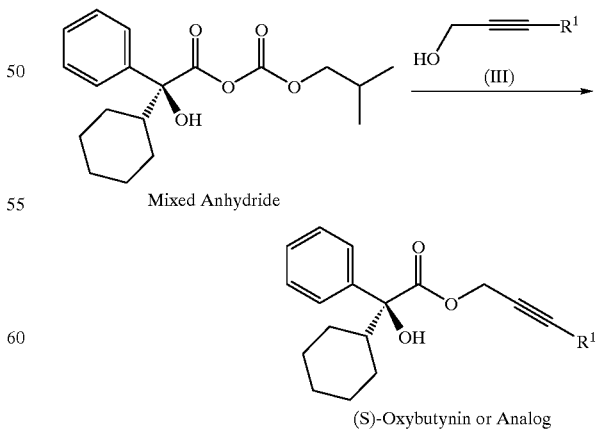

A sidechain propargyl alcohol derivative of formula (III), wherein $R^1$ is as previously defined, is added to the mixed anhydride contained in the reaction mixture to produce the single enantiomer of oxybutynin or analog thereof (II). About 1.3 equivalents of the formula (III) compound relative to (S) or (R)-CHPGA is sufficient. Typically, the reaction mixture is heated to reflux at a temperature of about 65–80° C., but more preferably about 70–75° C., until the reaction is complete, as determined by HPLC.

Most preferably, the propargyl alcohol derivative of formula (III) is a 4-amino propargyl alcohol derivative, wherein $R^1$ is represented as —$CH_2R^2$; $R^2$ is —$NR^3R^4$; and $R^3$ and $R^4$ are each independently hydrogen or a lower alkyl. For example, the compound of formula (III) is most preferably 4-N,N-diethylarnino butynol (4-N,N-DEB), where $R^3$ and $R^4$ are each ethyl. Reaction of the mixed anhydride with 4-N,N-DEB produces the single enantiomer of oxybutynin, i.e. (S) or (R)-4-diethylarmino-2-butynyl phenylcyclohexylglycolate. Another preferred embodiment is the reaction using 4-N-ethylamino butynol as the propargyl alcohol derivative to produce (S) or (R)-4-ethylamino-2-butynyl phenytcyclohexylglycolate, also known as desethyloxybutynin. In that case, $R^3$ is ethyl, and $R^4$ is hydrogen in formula (III). In another preferred embodiment, the propargyl alcohol derivative of formula (III) is 4-N,N-ethylmethylamino butynol, which results in the formation of (S) or (R)-4-ethylmethylamino-2-butynyl phenylcyclohexylglycolate. In this case, $R^3$ is ethyl, and $R^4$ is methyl.

Other useful sidechain propargyl alcohol compounds in which $R^1$ is —$CH_2R^2$ are those wherein $R^2$ is azide, hydroxy, or halo. In addition, propargyl alcohol itself, also known as 2-propyn-1-ol, may be reacted with the mixed anhydride. In this case, $R^1$ is hydrogen in formula (III).

4-N,N-Diethylamino butynol for use as the sidechain propargyl alcohol in the present invention may be prepared by reacting propargyl alcohol, paraformaldehyde, and diethylamine under standard Mannich conditions. Other amino and alkyl amino propargyl alcohol derivatives of structure (III) can be formed by the process disclosed in U.S. Pat. No. 5,677,346. Briefly, an amine or an alkyl amine containing p-methoxybenzyl as a protecting group, such as N-ethyl-4-methoxybenzenemethanamine for example, is reacted with propargyl alcohol and paraformaldehyde in the presence of cuprous chloride, followed by the addition of α-chloroethyl carbonochloridate to remove the protecting group. In this example, 4-N-ethylamino butynol is formed. The remaining propargyl alcohol derivatives for use in the present invention are commercially available or can be synthesized by methods known in the art.

As stated above, the progress of the condensation of the mixed anhydride with the propargyl alcohol may be conveniently monitored by periodic HPLC analyses of the reaction mixture until the desired extent of conversion is reached. At >80% conversion, the reaction is preferably quenched by washing with 10–12% aqueous monobasic sodium phosphate and water. About 8.5 g of the phosphate per gram of enantiomeric CHPGA used is typical. After separation of the organic phase, the aqueous washes are then discarded. A final wash using deionized water may then be performed, after which the bottom aqueous phase is discarded. The retained organic phase containing the enantiomer of structure (II) in solution with the organic solvent can then be concentrated to remove most of the solvent, typically by vacuum distillation.

Formation of the Hydrochloride Salt

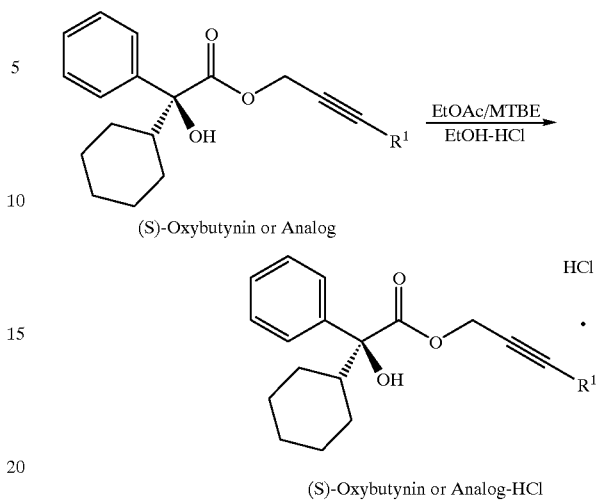

(S)-Oxybutynin or Analog (S)-Oxybutynin or Analog-HCl

To promote crystallization, the organic solvent containing the enantiomer of oxybutynin or one of its analogs (II) produced by the process outlined above (also referred to herein as "free base enantiomer (II)") is exchanged with ethyl acetate (EtOAc). Typically, the organic solvent is removed by vacuum distillation to contain about 20–25 wt % (S) or (R) enantiomer of structure (II), which is based on the theoretical amount of free base (II) formed from the coupling process above. Ethyl acetate is then added to obtain the original solution volume or weight. This step may be repeated substituting the removal of EtOAc for the organic solvent. The EtOAc solution may be filtered through a filtering agent, such as diatomaceous earth. The filter cake is washed with EtOAc as needed.

The filtrate is then concentrated by vacuum distillation, for example, to contain about 20–25 wt % (theoretical) of free base enantiomer (II) and ≦0.3 wt % water. To maximize product yield and purity and to encourage crystallization, most of the water should be removed from the solution. If the foregoing concentration processes are insufficient to reduce the water to ≦0.3%, the vacuum distillation may be repeated with fresh solvent or a drying agent, such as magnesium sulfate may be employed. Water content can be determined by KF (Karl Fisher method).

Methyl t-butyl ethyl (MTBE) is then added to the concentrated EtOAc solution to a volume that reduces the concentration by weight of the free base enantiomer (II) by about one third, or optimally to between about 6.5 and 8.5 wt %. The hydrochloride salt is then formed by the addition of HCl, while stirring. A slight excess of HCl in ethanol, for example about 1.1 equivalents of 35–40 wt % HCl, is generally sufficient. The temperature may be increased to 35–45° C.

To initiate recrystallization, the solution may be seeded with the hydrochloride salt of the enantiomer of structure (II). After about an hour of stirring, which may be done at 35–45° C., a slurry forms. If the slurry is cooled to about 0–5° C. and this temperature maintained for about two hours, filtration provides a very good recovery of the hydrochloride salt of the enantiomer of structure (II). The filter cake is typically a white to off-white crystalline solid, which can then be washed with ambient temperature methyl t-butyl ether (at least 2.2 g MTBE per gram free base enantiomer (II)), followed by vacuum drying at 40–50° C.

The following example is illustrative, but the present invention is not limited to the embodiment described therein:

EXAMPLE 2

Preparation of (S)-Oxybutynin-HCl

A 3-neck round bottomed flask was charged with 50.0 g (S)-CHPGA (213.0 mmol) and 780 g (1000 mL) cyclohexane under nitrogen. While stirring, 54 g triethylamine (2.5 equiv.) and 35 g isobutyl chloroformate (IBCF)(1.2 equiv.) were slowly added while maintaining the temperature at 20–30° C. After about 0.5 hour, while continuing to stir the reaction mixture, 39.15 g 4-N,N-DEB (1.3 equiv.) were added, and the mixture was heated to 65° C. to reflux. Mixing continued at reflux until the formation of (S)-oxybutynin was complete by HPLC area normalization.

Heating was discontinued, and the reaction mixture was cooled to between 20–30° C. At this time, 425 g of 11.5% $NaH_2PO_4.H_2O$ aqueous solution were added to the mixture, and the mixture was stirred for 10 min. Stirring was discontinued, and the organic and aqueous phases separated after about 15 minutes. The aqueous (bottom) phase was discarded. 425 g of 11.5% $NaH_2PO_4.H_2O$ aqueous solution were again added to the retained organic phase, and the mixture was stirred for about 10 min. The phases were then permitted to separate, which took about 15 minutes. The aqueous (bottom) phase was again discarded. To the remaining organic phase, deionized water (400 g) was added. The mixture was stirred for about 10 min, followed by phase separation after about 15 minutes. The aqueous (bottom) phase was discarded.

Cyclohexane was removed from the organic phase by vacuum distillation to about 350 g (~22 wt % (S)-oxybutynin based on the theoretical amount (76.29 g) of (S)-oxybutynin free base formed). Ethyl acetate (EtOAc) was added to obtain the original solution volume of about 1000 mL (or about 830 g), followed by vacuum distillation to 20–25 wt % (S)-oxybutynin. EtOAc was then added a second time to a volume of about 1000 mL (or about 830 g). The batch was then polish filtered through about 5.0 g CELITE® while washing the filter cake with EtOAc as needed. The filtered mixture was concentrated and dried by vacuum distillation to 339 g (~22.5 wt % (S)-oxybutynin) and ≦03 wt % water, as measured by KF.

Based on the theoretical amount of (S)-oxybutynin free base (76.29 g), methyl t-butyl ether was added to adjust the (S)-oxybutynin free base concentration to 8.0 wt % (953 g). With agitation, 23 g of 37 wt % HCl in EtOH (1.1 equiv.) were slowly added to the solution, while maintaining the temperature between 20 and 45° C. The temperature of the solution was then adjusted to 35–45° C., and the solution was seeded with about 500 mg (S)-oxybutynin-HCl crystals (approximately 10 mg of seeds per g (S)-CHPGA). The temperature was maintained, and the solution was stirred for about one hour. A slurry formed, which was then cooled to 0–5° C. over a minimum of 1 hour and held for 2 hours. The slurry was then filtered to recover the (S)-oxybutynin-HCl. The filter cake was a white to off-white crystalline solid. After washing with MTBE (a minimum of 167.84 g MTBE (2.2 g MTBE/g (S)-oxybutynin free base), the cake was dried in vacuo at 40–45° C. The residual solvent remaining in the cake was <0.5%. Dry weight=57.9 g. Overall yield= 68.9%.

EXAMPLE 3

Isolation of the two Carbonate Intermediates A and B

To a racemic mixture of cyclohexylphenylglycolic acid [CHPGA] (5.0 g, 0.0213mol) in cyclohexane (100 mL) was added triethylamine (7.4 mL, 0.053 mol) and isobutylchloroformate (5.5 mL, 0.0426 mol). The slurry was allowed to stir at ambient temperature for approximately 0.5 h, at which time the reaction was quenched with a 10% aq. $NaH_2PO_4$ (50 ml). The organic phase was separated from the aqueous phase and washed with 10% aq. $NaH_2PO_4$ (50 mL) followed by DI water (50 mL). The organic phase was dried over anhydrous $MgSO_4$ and concentrated in vacuo to afford a colorless oil. The product was purified by flash chromatography eluting with 95:5 hexane-EtOAc [$R_f$=0.2] to afford pure carbonate-anhydride A. The structure was confirmed by $^1H$ and $^{13}C$.NMR, IR, in situ IR and MS.

To a racemic mixture of cyclohexylphenylglycolic acid [CHPGA] (5.0 g, 0.0213 mol) in cyclohexane (100 mL) was added triethylamine (7.4 mL, 0.053 mol) or preferably 1-methyl piperidine (01053 mol), and isobutylchloroformate (3.3 mL, 0.026 mol). The slurry was allowed to stir at ambient temperature for approximately 0.5 h, at which time the reaction was quenched with a 10% aq. solution of $NaH_2PO_4$ (50 mL) followed by DI water (50 mL). The organic phase was dried over anhydrous $MgSO_4$ and concentrated in vacuo to afford a colorless oil as a 4:1 mixture of A and B by HPLC. The crude product was purified by passing the mixture through a plug of neutral alumina. Compound A was eluted first using $CHCl_3$. B was then washed off the alumina with acetone and concentrated in vacuo to afford pure carbonate-acid B. The structure was confirmed by $^1H$ and $^{13}C$ NMR, IR, in situ IR and MS.

While the invention has been particularly shown and described with reference to preferred embodiments thereof, it will be understood by those skilled in the art that the present disclosure is to be considered as an exemplification of the principles of this invention and is not intended to limit the invention to the embodiments illustrated.

We claim:

1. A compound of formula

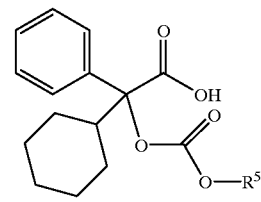

wherein $R^5$ is alkyl or alkenyl of one to ten carbons.

2. A compound according to claim 1 wherein $R^5$ is isobutyl.

3. A compound of formula

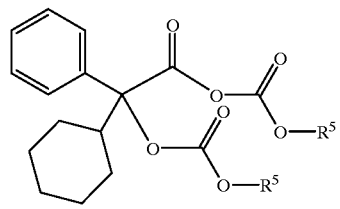

wherein $R^5$ is alkyl or alkenyl of one to ten carbons.

4. A compound according to claim 1 wherein $R^5$ is isobutyl.

* * * * *